United States Patent [19]

Johansson et al.

[11] Patent Number: 5,681,949

[45] Date of Patent: Oct. 28, 1997

[54] ALKYL GLYCOSIDE AND USE THEREOF

[75] Inventors: Ingegärd Johansson, Göteborg; Lennart Dahlgren, Ödsmål, both of Sweden

[73] Assignee: Akzo Nobel NV, Arnhem, Netherlands

[21] Appl. No.: 507,438

[22] PCT Filed: Mar. 10, 1994

[86] PCT No.: PCT/SE94/00199

§ 371 Date: Nov. 14, 1995

§ 102(e) Date: Nov. 14, 1995

[87] PCT Pub. No.: WO94/21655

PCT Pub. Date: Sep. 29, 1994

[30] Foreign Application Priority Data

Mar. 23, 1993 [SE] Sweden .................. 9300955

[51] Int. Cl.$^6$ .................. C07H 15/04; C11D 3/22
[52] U.S. Cl. .................. 536/123.1; 536/18.6; 252/174.17
[58] Field of Search .................. 536/120, 123, 536/123.1, 124, 18.6; 252/174.17

[56] References Cited

U.S. PATENT DOCUMENTS

| H171 | 12/1986 | McDaniel et al. | 252/174.17 |
|---|---|---|---|
| 3,772,269 | 11/1973 | Lew | 269/210 R |
| 3,839,318 | 10/1974 | Mansfield | 260/210 R |
| 4,713,447 | 12/1987 | Letton | 536/18.6 |
| 4,847,368 | 7/1989 | Barker et al. | 549/68 |
| 4,898,934 | 2/1990 | Lueders et al. | 536/18.6 |
| 4,990,605 | 2/1991 | Lueders et al. | 536/18.5 |
| 5,138,046 | 8/1992 | Wuest et al. | 536/18.6 |
| 5,449,763 | 9/1995 | Wulff et al. | 536/18.6 |
| 5,480,979 | 1/1996 | Weuthen et al. | 536/18.6 |
| 5,489,395 | 2/1996 | Behler et al. | 252/174.17 |
| 5,494,659 | 2/1996 | Salka et al. | 424/70.13 |
| 5,591,376 | 1/1997 | Kiewert et al. | 510/437 |

FOREIGN PATENT DOCUMENTS

| 0132043 | 1/1985 | European Pat. Off. . | |
|---|---|---|---|
| 0 306 650 B1 | 3/1989 | European Pat. Off. | C07H 15/04 |
| 0 306 651 A1 | 3/1989 | European Pat. Off. | C07H 15/04 |
| 0 306 652 B1 | 3/1989 | European Pat. Off. | C07H 15/04 |
| 0 387 912 A2 | 9/1990 | European Pat. Off. | C07H 15/04 |
| 20 36 472 B2 | 2/1971 | Germany | C07H 15/04 |

*Primary Examiner*—John Kight
*Assistant Examiner*—Howard C. Lee
*Attorney, Agent, or Firm*—Ralph J. Mancini; Louis A. Morris

[57] ABSTRACT

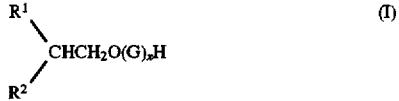

In an alkyl glucoside of formula (I) $R^1$ is an alkyl group having 2-5 carbon atoms, preferably 2-4 carbon atom; $R^2$ is an alkyl group having 4-7 carbon atoms, preferably 5 or 6 carbon atoms, the sum of the carbon atoms in $R^1$ and $R^2$ being 7-11, preferably 7-9; G is a monosaccharide residue; and x is 1-4, preferably 1 or 2. The use of the alkyl glucoside as a surfactant in a cleaning composition is also disclosed.

16 Claims, No Drawings

ALKYL GLYCOSIDE AND USE THEREOF

The present invention relates to a new alkyl glycoside presenting an advantageous combination of good cleaning power and low foaming, which renders it particularly suitable for cleaning hard surfaces.

In recent years, attention has focused on alkyl glycosides, since these have proved to be more easily biodegradable than other non-ionic surfactants, such as ethylene oxide adducts of fatty alcohols. U.S. Pat. No. 3,839,318 thus describes the production of alkyl glucosides and alkyl oligosaccharides, such as n-octyl glucoside, n-hexyl glucoside, n-decyl glucoside, n-dodecyl glucoside, isodecyl glucoside, isoundecyl glucoside, isotridecyl glucoside and the corresponding oligosaccharides. The U.S. Stationary Invention Registration H171 states that alkyl glycosides of formulae R(OG) and R(O)$_x$ are excellent surfactants. In these formulae, R is an alkyl or alkenyl group which is branched at the second carbon atom or at a higher carbon atom, the branch being selected from the group methyl, ethyl, isopropyl, n-propyl, butyl, pentyl, hexyl and mixtures thereof, provided that R contains from about 7 to about 30 carbon atoms; G is a saccharide group selected from the group glucose, fructose, mannose, galaclose, talose, allose, altrose, idose, arabinose, xylose, lyxose, ribose and mixtures thereof; and x is 2 or more. Example 1 contains a description of the production of two product mixtures substantially made up of 2-ethylhexyl glycoside and isooctyl glycoside, respectively.

DE 20 36 472, EP 306 650, EP 306 651 and EP 306 652, inter alia, also describe alkyl glucosides.

Even though alkyl glycosides generally are easily biodegradable, they are only used to a limited extent in many ranges of application, such as the cleaning of hard surfaces, since they are too high-foaming and/or have a poor cleaning power. Also, alkyl glycoside products containing branched alkyl groups often have a disagreeable smell. It is therefore a desideratum to provide non-ionic surfactants which are about as easily biodegradable, but which have a better cleaning power and/or are more low-foaming than known alkyl glycosides.

According to the invention, it has now surprisingly been found that an alkyl glycosides of the general formula

 (I)

wherein $R^1$ is an alkyl group having 2–5 carbon atoms, preferably 2–4 carbon atoms; $R^2$ is an alkyl group having 4–7 carbon atoms, preferably 5 or 6 carbon atoms, the sum of the carbon atoms in $R^1$ and $R^2$ being 7–11, preferably 7–9, G is a monosaccharide residue, and x is 1–4, preferably 1 or 2, has good cleaning and wetting properties and is low-foaming compared with other alkyl glycosides of approximately the same chain length. Compounds of formula (I) in which $R^1$ is an alkyl group having 3 carbon atoms, $R^2$ is an alkyl group having 5 carbon atoms, and G is a glucose residue, are especially preferred. The glycosides according to the invention do not have any disagreeable smell. In addition, they have been found to be easily degradable and have low biotoxicity. Tests have not shown any skin irritations caused by the alkyl glycosides.

The inventive compounds can be produced in conventional manner by reacting an alcohol of formula

 (II)

wherein $R^1$ and $R^2$ are as indicated above, with a monosaccharide, the molar ratio of the alcohol to the monosaccharide being 2:1–80:1, in the presence of an acid catalyst. The catalyst may be an inorganic or organic acid. The reaction is carried out under vacuum at 90°–120° C. for about 1–4 h. Conveniently, the resulting reaction mixture is first filtered and then neutralised with an organic and/or an inorganic base. Finally, excess alcohol is carefully removed, e.g. by distillation, if so desired.

The alcohols of formula (II) can be obtained by a Guerbet reaction starting from n-pentanol, n-hexanol or mixtures of n-pentanol and n-hexanol, n-pentanol and n-butanol, n-hexanol and n-butanol, and n-hexanol and n-pentanol, or by an aldol condensation of the corresponding aldehydes. Preferably, the alkanol of formula (II) is 2-propyl heptanol. The monosaccharide used as reactant suitably is pentose and hexose. Specific examples of monosaccharides used in the production of the inventive glucosides are glucose, mannose, galactose, talose, allose, altrose, idose, arabinose, xylose, ribose and lyxose. Glucose is usually preferred for commercial reasons.

The inventive alkyl glycosides are suitably used as surfactants in cleaning compositions, e.g. for degreasing hard surfaces or washing up. Excellent results are obtained in the degreasing of lacquered or unlacquered metal surfaces. Apart from the inventive alkyl glycosides, these compositions preferably contain a water-soluble solubiliser and suitably contain a complexing agent.

Examples of solubilisers are alkyl ether polyalkylene glycol, such as monobutyl diethylene glycol; glycols, such as diethylene glycol, dipropylene glycol and propylene glycol; alcohols, such as ethanol, propanol and isopropanol; alkyl glycosides in which the alkyl group has 4–18 carbon atoms; and/or tertiary or quaternary amine alkoxylates, in which the alkyl group, which may be straight or branched, saturated or unsaturated, has 8–20 carbon atoms, and 6–30 mol of alkylene oxide is added per mol of amine. Preferably, 50–100 mol percent of the added alkylene oxide consists of ethylene oxide, while the remaining amount preferably consists of propylene oxide or a mixture of propylene oxide and butylene oxide. The different alkylene oxides can be added randomly or in blocks. If the cleaning composition should be low-foaming, the alkylene oxide chain suitably ends with an addition of 1–5 mol of propylene oxide and/or butylene oxide. Usually, the ratio of solubiliser to the inventive alkyl glycoside is 1:10–5:1, preferably 1:3–3:1.

The complexing agent may be a conventional inorganic or organic complexing agent, such as an inorganic phosphate or NTA, EDTA, citric acid or a polycarboxylate. The amount added may vary from nothing at all to 300% by weight of the inventive alkyl glycoside. Preferably, the quantity ratio of the complexing agent to the alkyl glucoside is 1:10–2:1.

The cleaning compositions may further contain other additives, such as pH-adjusting agents, antifoaming agents, enzymes, other surfactants and scents. The compositions are usually aqueous and in the form of emulsions, microemulsions or solutions.

The invention will be further illustrated by the following Examples.

EXAMPLE 1

An alkyl glycoside was produced by reacting 3 mol of 2-propylheptanol with 0.45 mol of glucose in the presence of 0.015 mol of sulphuric acid as catalyst at 110° C. and 70 mbar. The reaction was interrupted after 65 min. The resulting product mixture was treated by distilling off excess alcohol under vacuum. The yield was 50 g, consisting of 74% of 2-propylheptyl monoglycoside, 15% of 2-propylheptyl diglucoside and a residue of higher oligomers. The glucosides had an average degree of polymerisation (DP) of about 1.3. The structure was determined by gas chromatography, mass spectrometry and NMR.

EXAMPLE 2

As in Example 1, 2-butyloctanol was reacted with glucose. The reaction temperature was 112° C., and the reaction time was 90 min. The average DP was 1.5.

EXAMPLE 3

Here, 20 ml of each of the cleaning compositions below, diluted with 10 parts by weight of water per part by weight of the composition, was applied to a vertically arranged iron sheet soiled with mineral oils, soot, salts and clay. After application, the coated surface was rinsed with water without any mechanical treatment.

| Components | Composition, % by weight ||||||||| 
|---|---|---|---|---|---|---|---|---|---|
| | 1 | 2 | 3 | 4 | A | B | C | D | E |
| Glucoside (Example 1) | 5 | 5 | 5 | | | | | | |
| Glucoside (Example 2) | | | | 5 | | | | | |
| Glucoside A | | | 8.5 | | 5 | | | | |
| Glucoside B | | | | | | 5 | | | |
| Glucoside C | | | | | | | 5 | | |
| Glucoside D | | | | | | | | 5 | |
| Butyldiethylene glycol | | 11 | | 11 | 11 | 11 | 11 | 11 | 11 |
| Quaternary ethoxylated fatty amine (Berol 555) | 4 | | | | | | | | |
| NTA | 5 | 5 | 3 | 3 | 3 | 3 | 3 | 3 | 5 |
| Water | 86 | 79 | 83.5 | 81 | 81 | 81 | 81 | 81 | 84 |

Glucoside A=2-ethylhexyl-O(G)$_x$H
Glucoside B=isooctyl-O(G)$_x$H
Glucoside C=n-dodecyl/n-tetradecyl glycoside (Plantaren, APG-600, Henkel)
Glucoside D=n-decyl glycoside (Lutensol GD-70, BASF)
G=glycoside residue and x=1.5 (average value).

The resulting cleaning effect was assessed with respect to the area of the cleaned surface, as well as the actual cleanness of this surface, the FIG. 1 indicating no improvement and the FIG. 10 indicating a perfectly clean surface. The following results were obtained.

| Composition | Cleaned surface, cm² | Cleanness |
|---|---|---|
| 1 | 88 | 8 |
| 2 | 120 | 8 |
| 3 | 128 | 8 |
| 4 | 112 | 8 |
| A | 0 | 1 |
| B | 80 | 4 |
| C | 48 | 6 |
| D | 72 | 6 |
| E | 0 | 1 |

The foaming of the different ready-to-use solutions was measured according to Ross-Miles ASTM D 1173-53. The following results were obtained.

| Composition | Foam height, mm ||
|---|---|---|
| | Instantaneously | After 5 min |
| 1 | 19 | 3 |
| 2 | 23 | 5 |
| 3 | 8 | 5 |
| 4 | 30 | 7 |
| A | 7 | 0 |
| B | 20 | 3 |
| C | 67 | 63 |
| D | 46 | 45 |

These results show that the alkyl glycosides according to the invention have an excellent cleaning power and are clearly superior to alkyl glycosides having a straight carbon chain with 10–14 carbon atoms, while at the same time showing an acceptable degree of foaming. The composition containing alkyl glycosides having an alkyl group with 8 carbon atoms shows an unsatisfactory cleaning power.

We claim:

1. An alkyl glycoside of the general formula

(I)

wherein R$^1$ is an alkyl group having 2–5 carbon atoms, R$^2$ is an alkyl group having 4–7 carbon atoms, the sum of the carbon atoms in R$^1$ and R$^2$ being 7–11, G is a monosaccharide residue, and x is 1–4.

2. The alkyl glycoside of claim 1, wherein R$^1$ is an alkyl group having 2–4 carbon atoms, and R$^2$ is an alkyl group having 4–6 carbon atoms, the sum of the carbon atoms in R$^1$ and R$^2$ being 7–9.

3. The alkyl glycoside of claim 1 wherein R$^1$ is an alkyl group having 3 carbon atoms and R$^2$ is an alkyl group having 5 carbon atoms.

4. The alkyl glycoside of claim 1 wherein G is a glucose residue.

5. The alkyl glycoside of claim 1 wherein x is 1 or 2.

6. A cleaning composition which comprises at least one alkyl glycoside in accordance with claim 1.

7. The composition of claim 6 which further comprises a water-soluble solubiliser and optionally an organic or inorganic complexing agent.

8. The composition of claim 7 wherein the solubilizer is selected from the group consisting of alkyl ether polyglycols, glycols, alcohols, tertiary alkylamine alkoxylates, quaternary alkylamine alkoxylates and mixtures thereof.

9. The composition of claim 8 which comprises a solubilizer in an amount of 1:3–3:1, based on the weight of the alkyl glycoside, and a complexing agent in an amount of 1:10–2:1, based on the weight of the alkyl glycoside.

10. A method for degreasing lacquered or unlacquered metal surfaces which comprises applying to said surfaces the composition of claim 7.

11. A process for preparing an alkyl glycoside of the formula:

(I)

wherein R$^1$ is an alkyl group having 2–5 carbon atoms, R$^2$ is an alkyl group having 4–7 carbon atoms, the sum of the carbon atoms in $R^1$ and $R^2$ being 7–11, G is a monosaccharide residue, and x is 1–4, which comprises reacting:

a) an alcohol of the formula

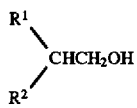 (I)

wherein $R^1$ is an alkyl group having 2–5 carbon atoms, $R^2$ is an alkyl group having 4–7 carbon atoms, the sum of the carbon atoms in $R^1$ and $R^2$ being 7–11, with b) a monosaccharide wherein said reaction is conducted in the process of an acid catalyst and wherein the ratio of alcohol to monosaccharide is from about 2:1 to about 80:1.

12. The process of claim 11 wherein said reaction is carried out under reduced pressure at a temperature of from 90° to 120° C.

13. The process of claim 11 wherein said alcohol is obtained by a Guerbet reaction starting from n-pentanol, n-hexanol, or mixtures thereof, n-pentanol and n-butanol, n-hexanol and n-butanol, and n-hexanol or n-pentanol.

14. The process of claim 11 wherein said alcohol is 2-propyl heptanol.

15. The process of claim 11 wherein said monosaccharide is selected from the group consisting of pentose, hexose, glucose, mannose, galactose, talose, allose, altrose, idose, arabinose, xylose, ribose, lyxose and mixtures thereof.

16. The process of claim 11 wherein $R^1$ is an alkyl group having 2–4 carbon atoms and $R^2$ is an alkyl group having 4–7 carbon atoms.

* * * * *